United States Patent [19]

Dornoff

[11] Patent Number: 6,077,503
[45] Date of Patent: Jun. 20, 2000

[54] SKIN WHITENER COMPOSITION CONTAINING MERCAPTODEXTRAN

[75] Inventor: Jeffrey M. Dornoff, Grand Rapids, Mich.

[73] Assignee: Amway Corporation, Mich.

[21] Appl. No.: 08/903,426

[22] Filed: Jul. 30, 1997

[51] Int. Cl.$^7$ ............................. A61K 7/48; A61K 7/40
[52] U.S. Cl. ............................. 424/62; 424/59; 514/844
[58] Field of Search ......................... 424/62, 59; 514/844

[56] References Cited

U.S. PATENT DOCUMENTS

| | | | |
|---|---|---|---|
| 4,818,768 | 4/1989 | Nazzaro-Porro . | |
| 4,827,016 | 5/1989 | Morgan | 560/16 |
| 5,527,509 | 6/1996 | Gibson | 422/56 |
| 5,683,705 | 11/1997 | Maes et al. | 424/401 |
| 5,710,177 | 1/1998 | Sauermann et al. | 514/557 |

FOREIGN PATENT DOCUMENTS

WO 95 34280  12/1995  WIPO .

OTHER PUBLICATIONS

Chemical Abstract No. 79062906; CA 79(11)62906q; Mercaptodextran, a metal–chelating and disulfide–reducing polythiol of high molecular weight; Author(s): Jellum, Egil; Aaseth, Jan; Eldjarn, Lorentz; Location: Rikshosp., Oslo, Norway; Journal: Biochem. Pharmacol.; Date: 1973; vol. 22; No. 10; pp. 1179–1188.

Mercaptodextran—a new copper chelator and scavenger of oxygen radicals; Aaseth, Jan; Benov, Ludmil; Ribarov, Stefan; Acta Pharmacologica Sinica; 1990; Jul.; 11(4): 363–367.

The Effect of Mercaptodextran and N–Acetylhomo–Cysteine on the Excretion of Mercury in Mice Exposed to Methyl Mercuric Chloride, J. Aaseth; T. Norseth; Commission of the European Communities, U.S. Environmental Protection Agency, World Health Organization, International Symposium Proceedings, *Recent Advances in the Assessment of the Health Effects of Environmental Pollution*; vol. II, Paris, Jun. 24 to 28, 1974; pp. 913–919.

The Effect of Mercaptodextran and N–Acetylhomocysteine on the Excretion of Mercury in Mice After Exposure to Methyl Mercury Chloride; Aaseth, Jan; Norseth, Tor; Journal: Acta Pharmacol Toxicol; vol. 35(1); pp. 23–32; Year: 1974.

The Effect of Mercaptodextran on Distribution and Toxicity of Mercury in Mice; Aaseth, Jan; Journal: Acta Pharmacol Toxicol; vol: 32(6): pp. 430–441; Year: 1973

*Primary Examiner*—Thurman K. Pace
*Assistant Examiner*—Brian K. Seidleck
*Attorney, Agent, or Firm*—Brinks Hofer Gilson & Lione; G. Peter Nichols

[57] ABSTRACT

A skin whitening composition includes mercaptodextran. The composition can be topically applied to the human skin and can include one or more whitening agents in combination with mercaptodextran to achieve enhanced whitening effect. A method of whitening human skin includes topically applying to the skin mercaptodextran in an amount and for a period of time sufficient to visibly whiten the skin. The method includes incorporating mercaptodextran with known whitening agents and applying to the skin in an amount and for a period of time sufficient to visibly whiten the skin.

14 Claims, No Drawings

SKIN WHITENER COMPOSITION CONTAINING MERCAPTODEXTRAN

BACKGROUND OF THE INVENTION

The present invention relates to a skin whitener composition containing mercaptodextran for external use and to a method of whitening skin by topically applying a composition containing an effective amount of mercaptodextran.

In Asia, most women desire whiter skin because of traditional beliefs that white skin denotes nobility and aristocracy. Skin color is primarily determined by the amount of melanin present in the skin. Thus, in recent years, cosmetic compositions have been developed to reduce the amount of melanin in the skin and therefore, whiten the skin. These development efforts have focused on whitening agents that inhibit the function and activity of tyrosinase, which plays a key role in the biosynthesis of melanin. For example, it has been proposed to incorporate into cosmetic compositions tyrosinase activity inhibitors such as hydroquinone, vitamin C and its derivatives, kojic acid, arbutin, glutathione, cysteine, and mulberry extract, among others.

In addition, thiolated materials such as mercaptosuccinic acid and mercaptoethanol have been proposed. The problem with these materials, however, is that due to the thiol moiety, the products have an objectionable odor that makes such a product undesirable to a consumer. Moreover, such materials are generally difficult to incorporate into water containing cosmetic formulations due to solubility difficulties.

Thus, despite the efficacy of the above compounds in producing a whiter skin, alternatives are continually being sought. The present inventor has now found that mercaptodextran is an effective skin whitening agent. Moreover, the mercaptodextran has a less objectionable odor and does not suffer from the solubility problems of the other known thiol containing whitening agents. It is also believed that the skin whitening effects of other known whitening agents can be enhanced by the addition of mercaptodextran.

SUMMARY OF THE INVENTION

It is an object of the present invention to provide compositions that include mercaptodextran, are suitable for external application, and prevent or inhibit the formation of melanin in the skin and thus whiten the skin. Another object is to enhance and accelerate the development of the whitening and beautifying effect exhibited by known whitening agents by adding mercaptodextran.

The present invention also includes a method of whitening the skin that comprises topically applying to the skin mercaptodextran in an amount and for a period of time sufficient to visibly whiten the skin. A preferred method comprises topically applying to the skin a composition, preferably a cosmetic composition, comprising mercaptodextran and, optionally, one or more known whitening agents.

The one or more known whitening agents may be selected from the group consisting of tyrosinase inhibitors, free radical scavengers, and mixtures thereof.

Examples of suitable tyrosinase inhibitors include, but are not limited to, kojic acid and its derivatives, arbutin and its derivatives, Licorice extract and its derivatives, ascorbic acid and its derivatives, and hydroquinone and its derivatives. Examples of suitable free radical scavengers include, but are not limited to Licorice extract and its derivatives, vitamin E and its derivatives, vitamin A and its derivatives, vitamin C and its derivatives, Rosemary extract and its derivatives, and superoxide dismutase. The mercaptodextran may also be combined with extracts or fermentates of acerola cherry.

In the whitener composition according to the present invention, the amount of mercaptodextran to be used can not be absolutely specified because it varies according to the form of preparation. However, it is generally used in an amount from about 0.01% to about 50%, more generally from about 0.01% to about 10%. Preferably the mercaptodextran is used in an amount from about 0.05% to about 2%, more preferably from about 0.1% to about 1% based on the whole weight of the whitener composition.

When the mercaptodextran is combined with known whitening agents, it is preferably combined such that the ratio of the mercaptodextran to the known whitening agent is from about 1:100 to about 100:1, preferably from about 1:50 to about 50:1, more preferably from about 1:10 to about 10:1. Most preferably, the ratio of mercaptodextran to known whitening agent is from about 1:5 to about 5:1.

It is noted that, unless otherwise stated, all percentages given in this specification and the appended claims refer to percentages by weight.

DETAILED DESCRIPTION OF THE INVENTION

In accordance with the present invention, a skin whitener composition is provided and comprises mercaptodextran as an active ingredient. In the whitener composition according to the present invention, the amount of mercaptodextran to be used can not be absolutely specified because it varies according to the form of the preparation. It is, however, generally used in an amount from about 0.01% to about 50%, more generally from about 0.01% to about 10%. Preferably the mercaptodextran is used in an amount from about 0.05% to about 2%, more preferably from about 0.1% to about 1% based on the whole weight of the whitener composition.

Mercaptodextran is a polythiol that can be synthesized by thiolating a dextran compound using for example N-acetylhomocysteine thiolactone. The dextrans may have any suitable molecular weight from about 500 to 500,000. The mercaptodextrans useful in the present invention can be prepared according to the method set forth in Eldjarn, L. & E. Jellum: Organomercurial-polysaccharide, a chromatographic material for the separation and isolation of SH-proteins; *Acta Chem. Scand.*, 17:2610–21 (1963), and/or Jellum, E., J. Aaseth & L. Eldjarn: Mercaptodextran, a metal chelating and disulphide-reducing polythiol of high molecular weight; *Biochem. Pharmacol.*, 22:1179–88 (1973), both which are incorporated herein by reference. Alternatively, it is believed that the mercaptodextran can be made by polymerizing the dextran with a sulfur derivative such as mercaptosuccinic acid. In any event, it is not presently believed that the method of manufacturing is critical to the practice of the present invention. Thus, the mercaptodextran can be prepared by any suitable method.

As noted above, since it is believed that the dextran can have any molecular weight from about 500 to about 500,000, the resulting mercaptodextran may also have any suitable molecular weight from about 500 to about 500,000 such that the mercaptodextran exhibits tyrosinase inhibition. In this regard, it is believed that the mercapotdextrans having a molecular weight less than about 100,000 may be more effect for skin whitening than those having a molecular weight greater than about 100,000. Consequently, it is preferred to use a mercaptodextran having a molecular weight between about 1000 and 100,000. In a preferred embodiment, a mercaptodextran from Pharmacia Biotech and having a molecular weight of about 10,000 was found to be effective.

In another aspect, the skin whitener composition comprises one or more whitening agents, and mercaptodextran to enhance the whitening effect of the whitening agents. In this other embodiment, the compositions of the present invention include mercaptodextran and one or more whitening agents. The whitening agents useful in the present invention are believed to include all the known whitening agents and those that may be developed in the future. Preferably, the whitening agents are selected from the group consisting of tyrosinase inhibitors, free radical scavengers, and mixtures thereof. Examples of suitable tyrosinase inhibitors include, but are not limited to, kojic acid and its derivatives, arbutin and its derivatives, licorice extract and its derivatives, ascorbic acid and its derivatives, and hydroquinone and its derivatives. Examples of suitable free radical scavengers include, but are not limited to, licorice extract and its derivatives, vitamin E and its derivatives, vitamin A and its derivatives, vitamin C and its derivatives, Rosemary extract and its derivatives and superoxide dismutase.

Although it may not be possible to identify and list all known whitening agents, the following whitening agents may be mentioned and for purposes of the present invention are preferred: extracts or fermentates of acerola cherry, hydroquinone, vitamin C and its derivatives, kojic acid and its derivatives, arbutin, bearberry extract, glutathione, lemon extract, cucumber extract, mulberry extract, licorice extract, and their derivatives. Preferred whitening agents are selected from the group consisting of kojic acid, derivatives of kojic acid, arbutin, derivatives of arbutin, bearberry extract, lemon extract, cucumber extract, vitamin C and its derivatives, extracts of acerola cherry and fermentates of acerola cherry.

The kojic acid or its esters may be represented by the formula:

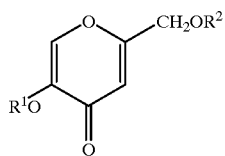

wherein $R^1$ and $R^2$ are the same or different, and each is hydrogen atom or an acyl group of 3 to 20 carbon atoms.

Non-exclusive examples of the esters are, for instance, kojic acid monoesters such as kojic acid monobutyrate, kojic acid monocaprate, kojic acid monopalmitate, kojic acid monostearate, kojic acid monocinnamoate and kojic acid monobenzoate; kojic acid diesters such as kojic acid dibutyrate, kojic acid dipalmitate, kojic acid distearate and kojic acid dioleate. A preferred monoester is an ester in which a OH group at 5-position of kojic acid is esterified. Esterification can improve stabilities against pH or sun light, while maintaining a melanin synthesis-inhibiting activity equal to that of kojic acid.

Non-exclusive examples of the vitamin C derivatives are, for instance, alkyl esters of L-ascorbic acid such as L-ascorbyl palmitate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate; phosphates of L-ascorbic acid such as L-ascorbyl-2-phosphate and L-ascorbyl-3-phosphate; sulfates of L-ascorbic acid such as L-ascorbyl-2-sulfate and L-acorbyl-3-sulfate; their salts with alkaline earth metals such as calcium and magnesium. They can be used alone or in a mixture of two or more.

When the mercaptodextran is mixed with the known whitening agents, the ratio of the mercaptodextran to the known whitening agent is from about 1:100 to about 100:1, preferably from about 1:50 to about 50:1, more preferably from about 1:10 to about 10:1. Most preferably, the ratio of mercaptodextran to known whitening agent is from about 1:5 to about 5:1.

It is believed that a composition containing mercaptodextran and one or more substances having a known whitening effect may exhibit synergism by enhancing the skin whitening effect of the known skin whiteners. It is believed that the mercaptodextran complexes with or chelates the copper present in tyrosinase and thus inhibits its synthesis. As a result the production of melanin is inhibited.

The compositions of the present invention may be prepared in various forms. For example, they may be in the form of a cosmetic preparation such as cream, cosmetic lotion, pack or powder, or as an emulsion, lotion, liniment foam, tablets, plasters, granules, or ointment. In each formulation, various known conventional cosmetic ingredients may be incorporated. For example, cosmetic ingredients such as alcohols, fats and oils, surfactants, fatty acids, silicone oils, humectants, moisturizers, viscosity modifiers, emulsifiers, stabilizers, coloring agents, and perfumes may be included.

In another aspect of the composition of the present invention there is provided an improved skin whitening composition of the type containing skin whitening agents wherein the improvement comprises adding mercaptodextran.

The present invention also contemplates a method of enhancing the skin whitening effect of known whitening agents that comprises adding mercaptodextran to a composition containing the known whitening agents.

In another aspect of the present invention, a method of whitening skin is provided and comprises topically applying to the skin mercaptodextran in an amount and for a period of time sufficient to visibly whiten the skin. More preferably, the method comprises topically applying to the skin a composition comprising mercaptodextran and a pharmaceutically acceptable carrier. The term "pharmaceutically acceptable" means those drugs, medicaments, or inert ingredients which are suitable for use in contact with the tissues of humans and lower animals without undue toxicity, incompatibility, instability, irritation, and the like, commensurate with a reasonable benefit/risk ratio.

To demonstrate the effectiveness of the mercaptodextran according to the present invention, the following test was conducted.

A buffer solution A containing 50 mM sodium acetate was prepared to yield a 6.8 pH. A tryosine solution was prepared by adding 15 mg of tyrosine to 100 ml of buffer solution A. A tyrosinase solution was prepared by adding 11.5 mg tyrosinase from mushroom (Serva Art. 37618, 72 $\mu$/mg) in 1.2 ml. of buffer solution A.

A test tube was charged with 2.7 ml of buffer solution A and 0.4 ml. water to define a blank. Similarly, another test tube was charged with 2.7 ml. of the tyrosine solution, 0.3 ml of water, and 0.1 ml of the tyrosinase solution to define a reference. The samples were stored for 24 hours at a temperature between 23° C. and 25° C. The absorbency of the reference was measured at 475 nm with a spectrophotometer and the absorbancy was set to zero.

The following examples present the results of the inhibition of the tyrosinase as measured in the above manner by several whitening agents, including the mercaptodextran.

EXAMPLE 1

A test tube was charged with 2.7 ml of the tyrosine solution, 0.1 ml. of the tyrosinase solution and 1% mercaptodextran having a molecular weight of about 10,000 from Pharmacia Biotech. The sample was stored for 24 hours at a temperature between 23° C. and 25° C. The absorbancy of was measured at 24 hours. The percent inhibition of the tyrosinase of was calculated as follows:

$$\% \text{ inhibition} = 100 \times \left[ 1 - \frac{\left( \begin{array}{c} \text{absorbancy of} \\ \text{Example 1} \end{array} - \begin{array}{c} \text{absorbancy of} \\ \text{reference} \end{array} \right)}{\begin{array}{c} \text{absorbancy} \\ \text{of reference} \end{array} - \begin{array}{c} \text{absorbancy of} \\ \text{blank} \end{array}} \right]$$

The percent inhibition was 90.2% at 24 hours.

Table 1 compares percent inhibition at 24 hours of other known whitening agents with the mercaptodextran in the manner described in Example 1.

TABLE 1

| Whitener | concentration (wt %) | Percent inhibition (24 hours) |
|---|---|---|
| Kojic Acid | 1.0 | 87.8 |
| Uninontan (commercial product containing lemon and cucumber extract) | 1.0 | 14.1 |
| Tioxolone | 1.0 | 0.0 |
| Example 1 | 1.0 | 90.2 |

EXAMPLE 2

In the following example, different concentrations of mercaptodextran (having a molecular weight of about 10,000 from Pharmacia Biotech) were compared to a constant concentration of two known whitening agents in the manner described above. Table 2 presents the results.

TABLE 2

| Whitening Agent | Concentration (wt %) | Percent Inhibition (24 hours) |
|---|---|---|
| Kojic Acid | 1.0 | 90.9 |
| Uninontan | 1.0 | 58.2 |
| Mercaptodextran | 1.0 | 91.9 |
| Mercaptodextran | 0.5 | 92.9 |
| Mercaptodextran | 0.2 | 56.9 |

Based on the above tests it is believed that compositions containing mercaptodextran would be efficacious in whitening skin.

EXAMPLE 3

The following is an example of a composition according to the present invention.

| INGREDIENT | PERCNETAGE (weight) |
|---|---|
| Water | 89.11 |
| Carbopol 1342 | 0.20 |
| Glycerin | 4.80 |
| Triethanolamine | 0.20 |
| Squalane | 3.00 |
| Sorbitan Laurate | 0.20 |
| Soybean Oil | 1.00 |
| Mercaptodextran | 1.00 |
| Phenonip | 0.50 |

EXAMPLE 4

The following is an example of an oil-in-water emulsion composition according to the present invention.

| INGREDIENT | PERCENTAGE (weight) |
|---|---|
| WATER PHASE | |
| Water | 71.33 |
| Butylene Glycol | 4.00 |
| Acerola Cherry Fermentate | 0.50 |
| OIL PHASE | |
| Meadowfoam Seed Oil | 1.00 |
| Isopropyl Myristate | 1.50 |
| C12–15 Alkyl Benzoate | 2.00 |
| Dimethicone | 1.00 |
| Isostearoyl Palmitate | 3.00 |
| Arlacel 165 | 5.00 |
| Sorbitan Stearate | 1.00 |
| Behenyl Alcohol | 2.50 |
| POST PHASE COMBINATION | |
| Uninontan | 0.50 |
| Orange Extract | 0.50 |
| Mercaptodextran | 2.00 |
| Cucumber Extract | 0.50 |
| Adjuvants | 3.67 |

It should be understood that a wide range of changes and modifications can be made to the embodiments described above. It is therefore intended that the foregoing description illustrates rather than limits this invention, and that it is the following claims, including all equivalents, which define this invention.

What is claimed:

1. A topical cosmetic composition having melanin synthesis-inhibiting activity comprising mercaptodextran and one or more cosmetic ingredients selected from the group consisting of alcohols, fats, oils, surfactants, fatty acids, silicone oils, humectants, moisturizers, viscosity modifiers, emulsifiers, stabilizers, coloring agents, and perfumes.

2. The composition of claim 1 wherein the mercaptodextran is present in an amount from about 0.01 to about 50%, by weight.

3. The composition of claim 1 wherein the mercaptodextran has a molecular weight from about 500 to about 500,000.

4. The composition of claim 1 which is a preparation selected from the group consisting of cream, ointment, foam, lotion, plaster, tablets, granules, or emulsion.

5. The composition of claim 2 further comprising a skin whitening agent selected from the group consisting of tyrosinase inhibitors, free radical scavengers, and mixtures thereof.

6. The composition of claim 5 wherein the ratio of the mercaptodextran to the skin whitening agent is from about 100:1 to about 1:100.

7. In a topical skin whitening cosmetic composition containing one or more cosmetic ingredients selected from the group consisting of alcohols, fats, oils, surfactants, fatty acids, silicone oils, humectants, moisturizers, viscosity modifiers, emulsifiers, stabilizers, coloring agents, and perfumes, the improvement comprising an effective amount of mercaptodextran to whiten the skin.

8. A method of visibly whitening human skin comprising topically applying to the skin mercaptodextran in an amount and for a period of time sufficient to visibly whiten the skin.

9. The method of claim 8 wherein the mercaptodextran is incorporated into a cosmetic preparation selected from the group consisting of cream, ointment, foam, lotion, plaster, tablets, granules, or emulsion.

10. The method of claim 9, wherein the mercaptodextran is present in the cosmetic preparation in an amount from about 0.01% to about 50%, by weight.

11. The method of claim 10 wherein the cosmetic preparation further comprises a skin whitening agent selected from the group consisting of tyrosinase inhibitors, free radical scavengers, and mixtures thereof.

12. The method of claim 11 wherein the ratio of the mercaptodextran to the skin whitening agent is from about 100:1 to about 1:100.

13. A topical composition comprising;

a. from about 0.01% to about 50% by weight of a mercaptodextran having a molecular weight from about 500 to about 500,000; and b. a skin whitening agent selected from the group consisting of tyrosinase inhibitors, free radical scavengers, and mixtures thereof, wherein the free radical scavengers are selected from the group consisting of licorice extract and its derivatives, vitamin E and its derivatives, vitamin A and its derivatives, vitamin C and its derivatives, Rosemary extract and its derivatives, and superoxide dismutase and wherein the ratio of the mercaptodextran to the skin whitening agent is from about 100:1 to 1:100.

14. A topical oil-in-water emulsion comprising water, a surfactant, an oil, and an effective amount of mercaptodextran to whiten the skin.

\* \* \* \* \*